(12) United States Patent
Razavi et al.

(10) Patent No.: US 11,628,185 B2
(45) Date of Patent: Apr. 18, 2023

(54) STABILIZED ACTIVE OXYGEN-GENERATING ANTISEPTIC COMPOSITIONS, IRRIGATION SOLUTIONS, AND ARTICLES

(71) Applicant: OXION DENTAL, LLC, Newtown, PA (US)

(72) Inventors: Ali Razavi, Dallas, PA (US); Farid Razavi, Downington, PA (US); Anthony Andrew Prousi, Newtown, PA (US)

(73) Assignee: OXION DENTAL, LLC, Newtown, PA (US)

(*) Notice: Subject to any disclaimer, the term of this patent is extended or adjusted under 35 U.S.C. 154(b) by 0 days.

(21) Appl. No.: 17/651,363

(22) Filed: Feb. 16, 2022

(65) Prior Publication Data
US 2022/0257644 A1 Aug. 18, 2022

Related U.S. Application Data

(60) Provisional application No. 63/150,241, filed on Feb. 17, 2021.

(51) Int. Cl.
*A61K 33/04* (2006.01)
*A61P 31/04* (2006.01)
*A61K 9/00* (2006.01)
*A61K 9/08* (2006.01)

(52) U.S. Cl.
CPC ............ *A61K 33/04* (2013.01); *A61K 9/0014* (2013.01); *A61K 9/0024* (2013.01); *A61K 9/08* (2013.01); *A61P 31/04* (2018.01)

(58) Field of Classification Search
CPC ........ A61K 33/04; A61K 9/0024; A61P 31/04
See application file for complete search history.

(56) References Cited

U.S. PATENT DOCUMENTS

| | | | |
|---|---|---|---|
| 4,438,144 A | 3/1984 | Blackburn | |
| 5,006,571 A * | 4/1991 | Kumar | C09J 101/26 523/120 |
| 5,186,946 A * | 2/1993 | Vallieres | A01N 37/00 424/613 |
| 5,284,647 A | 2/1994 | Niedballa et al. | |
| 5,436,228 A | 7/1995 | Postlethwaite et al. | |
| 5,736,165 A | 4/1998 | Ripley et al. | |
| 6,361,551 B1 | 3/2002 | Torgerson et al. | |
| 6,767,891 B2 | 7/2004 | Zaveri | |
| 7,160,553 B2 | 1/2007 | Gibbins et al. | |
| 7,959,617 B2 * | 6/2011 | Rucinski | A61M 35/00 604/310 |
| 8,679,523 B2 | 3/2014 | Gibbins et al. | |
| 9,468,654 B1 * | 10/2016 | Razavi | A61K 33/40 |
| 2002/0103503 A1 | 8/2002 | Torgerson et al. | |
| 2003/0091601 A1 | 5/2003 | Barbul | |
| 2010/0158818 A1 | 6/2010 | Jain et al. | |
| 2011/0229583 A1 | 9/2011 | Tran et al. | |
| 2012/0074014 A1 | 3/2012 | Tran et al. | |
| 2013/0157949 A1 | 6/2013 | Al-Mahmood et al. | |
| 2013/0209575 A1 * | 8/2013 | Squire | A01N 59/02 |
| 2013/0288965 A1 | 10/2013 | Bolscher et al. | |
| 2013/0296530 A1 | 11/2013 | Bolscher et al. | |
| 2014/0120153 A1 | 5/2014 | Gibbins et al. | |
| 2017/0367943 A1 * | 12/2017 | Johansson | A61K 8/23 |
| 2020/0138682 A1 * | 5/2020 | Galiyara | A61K 8/22 |

FOREIGN PATENT DOCUMENTS

| | | | | |
|---|---|---|---|---|
| CN | 110642296 A | * | 1/2020 | ............. C01G 45/02 |
| CN | 110786339 A | * | 2/2020 | ............. A01N 59/02 |
| CN | 110786339 A | | 2/2020 | |
| EP | 0395902 A2 | | 11/1990 | |
| WO | 2011157716 A1 | | 12/2011 | |
| WO | 2012060832 A1 | | 5/2012 | |
| WO | 2018052443 A1 | | 3/2018 | |

OTHER PUBLICATIONS

CN110642296A, Google English Translation, downloaded in May 2022 (Year: 2022).*
Christian Laurence E. Aquino et al, Effect of ammonium persulfate on the growth of MnO2 nanostructures prepared via hydrothermal synthesis for supercapacitor applications, Materials Today: Proceedings 33 (2020) 1945-1948 (Year: 2020).*
Guangfeng Xiao et al, Evolution of Singlet Oxygen by Activating Peroxydisulfate and Peroxymonosulfate: A Review, Int. J. Environ. Res. Public Health 2021, 18, 3344 (Year: 2021).*
CN110786339A, Google English Translation Document, downloaded in Mar. 2023 (Year: 2023).*
Hussain et al. "Journey Describing Applications of Oxone in Synthetic Chemistry" Chemical Reviews, American Chemical Society, 2013, 113, 3329-3371, ACS Publications, pubs.acs.org/CR.
Dupont, Material Safety Data Sheet, "Oxone® Monopersulfate compound", Version 2.0, Revision Date May 11, 2011, Ref. 130000000134, pp. 1-8.

(Continued)

Primary Examiner — Mark V Stevens
Assistant Examiner — Alparslan Asan
(74) Attorney, Agent, or Firm — McNees Wallace & Nurick LLC

(57) ABSTRACT

A stabilized active oxygen-generating antiseptic composition is disclosed including at least one of an antiseptic mixture or an antiseptic polymer. The antiseptic mixture includes a persulfate distributed in a matrix of a sulfate wherein the antiseptic composition is characterized by a ratio of the sulfate to the persulfate of at least 8:2. The antiseptic polymer is formed by the reaction of a sulfate, a persulfate, and amino acid in a reaction solution having a ratio of the sulfate to the persulfate of at least 6:4 and a ratio of the amino acid to the sulfate and the persulfate combined of 1:2 to 2:1. An antiseptic irrigation solution is disclosed including the antiseptic composition dispersed in a solvent. An antiseptic article is disclosed including an article and at least one of the antiseptic composition or an antiseptic coating formed from the antiseptic composition disposed on a surface of the article.

27 Claims, 5 Drawing Sheets

(56) References Cited

OTHER PUBLICATIONS

Sigma-Aldrich, Safety Data Sheet, "Potassium monopersulfate triple salt", Version 3.10, Revision Date Jul. 1, 2014, pp. 1-8.
"The Ultimate Formula for Advanced Wound Care," Nutrica Advanced Medical Nutrition, dated Sep. 2011, 4 pgs.
"Infection Reistant Coating," SPI-ARGENT™, undated, obtained Oct. 2014, 2 pgs.
O. Ermer and C. Robke, Crystal Structure and Chemical Stabilization of the Triple Salt (KHSO5)2 (KHSO4) (K2SO4), Institut for Organische Chemie der Univsrsitat, pp. 2908-2913, Received May 9, 2003.
Kimberly-Clark Health Care/OxyGenesys, pp. 1-4, Oct. 13, 2014, http://www.kchealthcare.com/products/surgical-solutions/oxygenesys.aspx.
N. Variankaval et al., "From Form to Function: Crystallization of Active Pharmaceutical Ingredients," AIChE Journal, Jul. 2008, vol. 54, No. 7, pp. 1682-1688.
A.E. Golovinsky, "RP-HPLC Analysis of Amino Acids With UV-Detection," Bulgarian Academy of Sciences, Provided by the NASA Astrophysics Data System, vol. 56, No. 12, 2003, pp. 75-78.
G. Maggio, et al., "A new protocol for the treatment of the chronic venous ulcers of the lower limb," PubMed Mobile-NCBI, pp. 1-2, May 2011, http://www.ncbi.nlm.nih.gov/m/pubmed/21559987/.
Kannan et al. Studies on the Autocatalyzed Oxidation of Amino Acids by Peroxomonosulfate, Int. Chem. Kinet. (2003), vol. 35. pp 475-483.
Ecodcid (R) S Technical Presentation (2009).
Dvorak, Disinfection 101, Center for Food Security and Public Health (2008), pp. 1-20.
LoPachin et al., Molecular Mechanisms of Aldehyde Toxicity: A Chemical Perspective, Chemical Research in Toxicology (2014), vol. 27, pp. 1081-1091.
Ramachandran et al., Kinetics and Mechanism of the Oxidation of Amino Acids by Peroxomonosulphate, Part 1., J. Chem. Soc. Perkin Trans. 11 (1984), pp. 1341-1344.
Wu et al., Reactive Impurities In Excipients: Profiling, Identification and Mitigation of Drug-Excipient Incompatibility, AAPS PharmScitTech (2011), vol. 12, No. 4, pp. 1248-1263.
PCT International Search Report and Written Opinion of the International Searching Authority issued to counterpart Application No. PCT/US2022/016619 dated May 6, 2022.

\* cited by examiner

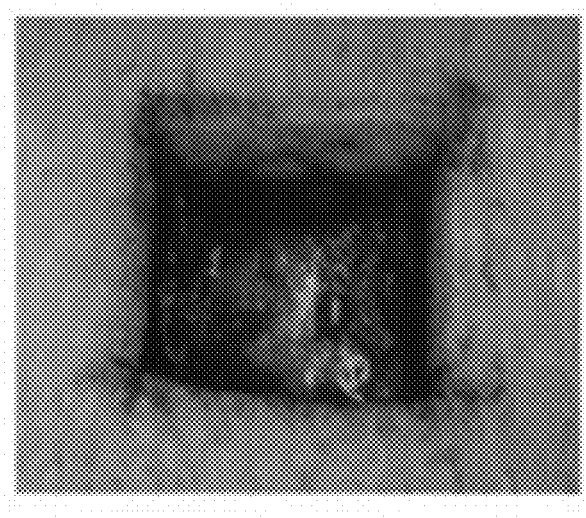 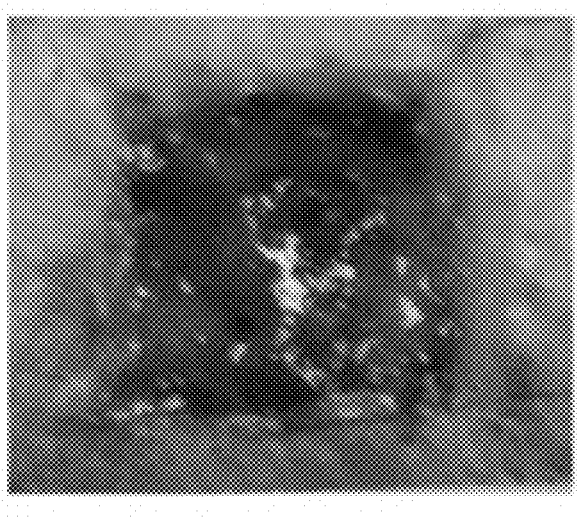
FIG. 4A                                    FIG. 4B

STABILIZED ACTIVE OXYGEN-GENERATING ANTISEPTIC COMPOSITIONS, IRRIGATION SOLUTIONS, AND ARTICLES

CROSS-REFERENCE TO RELATED APPLICATIONS

This application claims the benefit of U.S. Provisional Patent Application No. 63/150,241, filed Feb. 17, 2021, entitled "Stabilized Active Oxygen-Generating Antiseptic Compositions, Irrigation Solutions, and Implants," the disclosures of which are incorporated by reference in their entirety and made part of the present U.S. non-provisional utility patent application for all purposes.

FIELD OF THE INVENTION

This application is directed to stabilized active oxygen-generating antiseptic compositions, irrigation solutions, and implants. More specifically, this application is directed to stabilized active oxygen-generating antiseptic compositions, irrigation solutions, and implants derived from sulfates, persulfates, and, in some embodiments, amino acids.

BACKGROUND OF THE INVENTION

Wound lavage is a key aspect of reducing post-operative infections. Well known for over a century, intra-operative wound irrigation reduces rates of infection via removal of debris, reduction of bacterial load, reduction of metabolic waste, and removal of wound exudate.

Wound lavage is described by three primary variables: the volume of the irrigation fluid; the mechanism/timing of delivery (pressure and distribution); and the composition of the irrigation fluid itself. The composition of the irrigation fluid is typically selected so as to present antibiotic, surfactant, or antiseptic properties. Antibiotic irrigation fluids may be quite effective, particularly where a specific antibiotic for an identified microorganism which is not drug resistant is applied. However, antibiotic irrigation fluids tend to be high cost, are subject to and may lead to development of antibiotic resistance, and are typically characterized by slow onset to action. Surfactant irrigation fluids are problematic in that they may have detrimental effects on osteoblast/osteoclast cell lines, and it is known that bacterial counts may significantly rebound following lavage. Antiseptic irrigation fluids have potentially excellent characteristics for lavage, including for orthopedic and general surgical site infection. However, known antiseptic irrigation fluids are either deficient in anti-microbial activity or have detrimental effects, such as causing damage to live tissue, which are unacceptable.

The current standard wound lavage in use, which was invented in 1955, is povidone-iodine, which has equivocal benefits, limited data, and known metabolic toxicity. Indeed, a systematic review and meta-analysis published in March 2020 shed doubt on the efficacy of povidone-iodine, revealing that in seven studies with 31,213 TJA cases there were no differences in post-operative infection rates between povidone-iodine and non-povidone-iodine lavage groups. Similarly, recent Mayo Clinic case series reported no risk reduction effect of povidone-iodine lavage on post-operative infection in a large combined series of more than 10,000 THAs and TKAs. Despite the lack of evident effectiveness, povidone-iodine also has significant negative effects, including inhibiting cell migration and survival of osteoblasts, fibroblasts, and myoblasts. At all tested concentrations, povidone-iodine, even at a dilute 0.35%, produces a pronounced chondrotoxic effect when used for more than 1 minute, necessitating washing out of the application site following use. Topical application of povidone-iodine prior to wound closure is associated with significant increases in serum iodine level.

Triple salts are known to disassociate highly reactive oxygenated species when exposed to elevated moisture levels and may approximate the effects of naturally occurring oxidative bursts. However, triple salts possess only limited antimicrobial activity, due in part to the very slow rate of solid to liquid transformation of triple salts when exposed to elevated levels of moisture. Further, triple salts have limited shelf life and may contain hazardous impurities, including, but not limited to, irritants.

Accordingly, it would be desirable to provide antiseptic compositions which overcome the above-described deficiencies.

BRIEF DESCRIPTION OF THE INVENTION

In one exemplary embodiment, a stabilized active oxygen-generating antiseptic composition includes at least one of an antiseptic mixture or an antiseptic polymer. The antiseptic mixture includes a matrix of a first sulfate and a first persulfate distributed in the matrix of the first sulfate, wherein the antiseptic composition is characterized by a ratio of the first sulfate to the first persulfate of at least 8:2. The antiseptic polymer is formed by the reaction of a second sulfate, a second persulfate, and amino acid in a reaction solution having a ratio of the second sulfate to the second persulfate of at least 6:4 and a ratio of the amino acid to the second sulfate and the second persulfate combined of 1:2 to 2:1.

In another exemplary embodiment, an antiseptic irrigation solution includes a stabilized active oxygen-generating antiseptic composition and a solvent in which the stabilized active oxygen-generating antiseptic composition is dispersed. The antiseptic composition includes at least one of an antiseptic dispersal of a first sulfate and a first persulfate characterized by a ratio of the first sulfate to the first persulfate of at least 8:2 or an antiseptic polymer formed by the reaction of a second sulfate, a second persulfate, and amino acid in a reaction solution having a ratio of the second sulfate to the second persulfate of at least 6:4 and a ratio of the amino acid to the second sulfate and the second persulfate combined of 1:2 to 2:1.

In yet another exemplary embodiment, an antiseptic article includes an article (having a surface) and at least one of a stabilized active oxygen-generating antiseptic composition or an oxygen-generating antiseptic coating formed from the stabilized active oxygen-generating antiseptic composition disposed on the surface of the article. The stabilized active oxygen-generating antiseptic composition includes at least one of and antiseptic mixture or an antiseptic polymer. The antiseptic mixtures includes a matrix of a first sulfate and a first persulfate distributed in the matrix of the first sulfate, wherein the antiseptic composition is characterized by a ratio of the first sulfate to the first persulfate of at least 8:2. The antiseptic polymer is formed by the reaction of a second sulfate, a second persulfate, and amino acid in a reaction solution having a ratio of the second sulfate to the second persulfate of at least 6:4 and a ratio of the amino acid to the second sulfate and the second persulfate combined of 1:2 to 2:1.

BRIEF DESCRIPTION OF THE DRAWINGS

FIGS. 4A (initial) and 4B (following treatment) show the effects of stabilized oxygen-generating antiseptic composition in powder form dissolved in deep wounds in porcine tissue, according to an embodiment of the invention.

Wherever possible, the same reference numbers will be used throughout the drawings to represent the same parts.

DETAILED DESCRIPTION OF THE INVENTION

Figure 1:
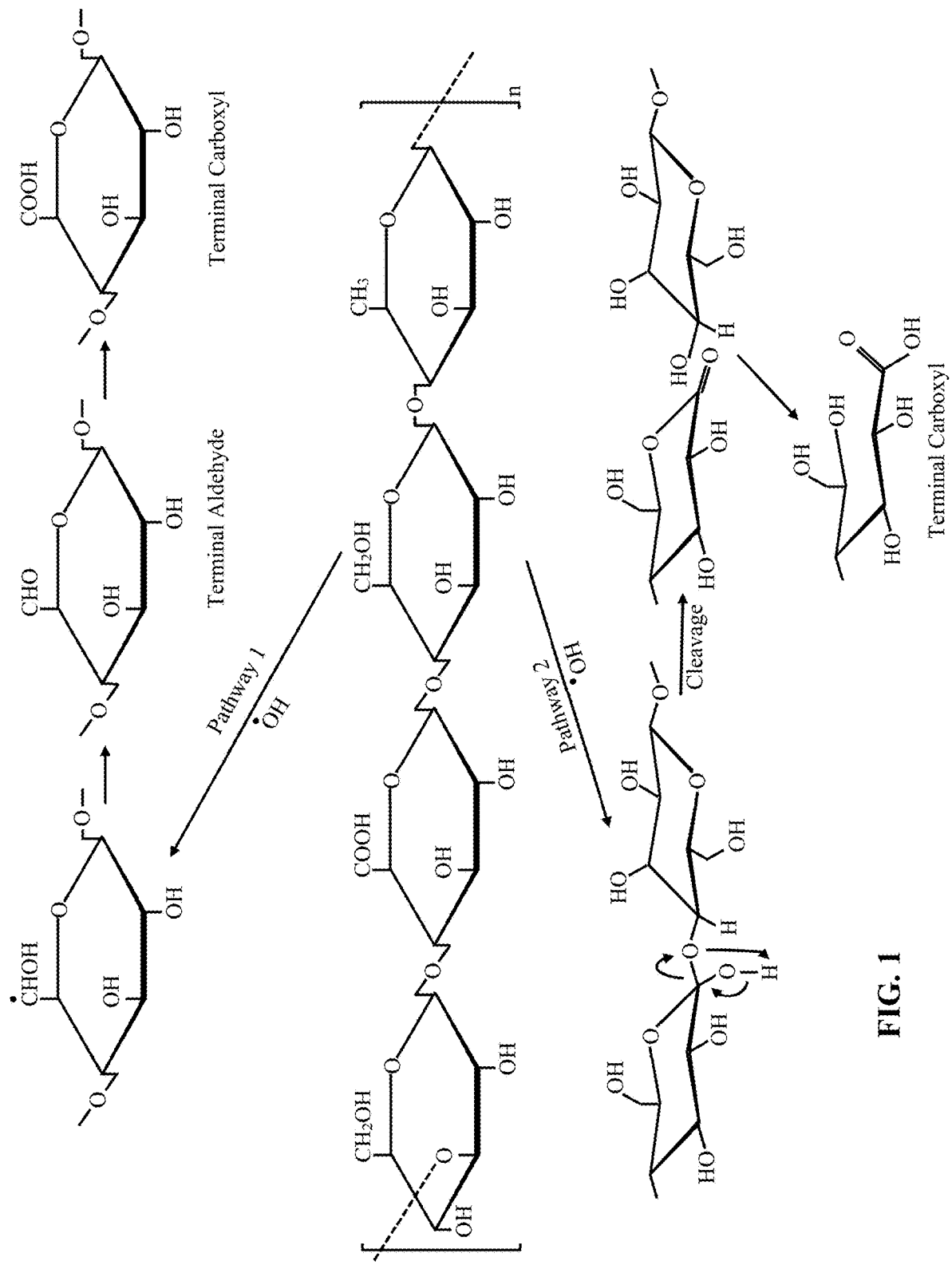
FIG. 1 presents a mechanism for the oxidation of glycosidic linkages in polysaccharides.

The stabilized active oxygen-generating antiseptic compositions, antiseptic irrigation solutions, antiseptic articles, and antiseptic implants disclosed herein provide robust anti-microbial activity with reduced or no detrimental effects, such as inducing damage to live tissue in comparison to antiseptic compositions lacking the features disclosed herein, are free of cytotoxic effects on human tissues, are free of local toxicity to human tissue, are free of systemic toxicity to human tissue, avoid or eliminate any need to washout an application site after application, provide broad bactericidal activity to reduce or eliminate even challenging pathogens (ESKAPE) in surgical site infections without microbial resistance, provide fungi and viral broad eradication capacity without developing resistance, provide capacity to design and control kinetic release of active oxygen, are suitable for being provided terminally sterile for operating room use, or combinations thereof.

Microbes produce a biofilm matrix consisting of bacterial extracellular polysaccharide polymer protecting the bacterium within. A chronic wound, such as a surgical wound, is a wound that is arrested in the inflammatory phase of wound healing and cannot progress further. Over 90% of chronic surgical wounds contain bacteria living within a biofilm. Disruption of biofilm extracellular matrices and eradication of surgical biofilms is a major healthcare challenge. Depolymerization of biofilm protective polysaccharide polymer structures by selective oxidation of glycosidic linkage to form glucose monomer to form glucose monomer, and eradication of bacteria within the biofilm may be achieved in the present invention by an active oxygen release mechanism.

Inventive stabilized active oxygen-generating antiseptic compositions and irrigation solutions may remain on a wound site and deliver active oxygen for more than three days. Inventive stabilized active oxygen-generating antiseptic compositions and irrigation solutions may provide effective tissue regeneration by active oxygen and extracellular matrix formation in liquid for cell attachments. Low concentration of active oxygen from stabilized active oxygen-generating antiseptic compositions and irrigation solutions may delver unmet properties to all types of wounds, including, but not limited to, surgical wounds and procedures, nostrils and oral sites, colorectal surgical sites, traumatic wounds, burns, lacerations, diabetic wounds, combat wounds, acute wounds, and chronic wounds.

As used herein, "active" oxygen refers to an oxygen species which is less stable than, and hence more active than, ground state triplet $O_2$. Active oxygen species include, but are not limited to, singlet $O_2$, ozone, superoxide, and peroxide.

In one embodiment, a stabilized active oxygen-generating antiseptic composition includes at least one of an antiseptic mixture or an antiseptic polymer. The antiseptic mixture includes a matrix of a first sulfate and a first persulfate distributed in the matrix of the first sulfate, wherein the antiseptic composition is characterized by a ratio of the first sulfate to the first persulfate of at least 8:2. The antiseptic polymer is formed by the reaction of a second sulfate, a second persulfate, and amino acid in a reaction solution having a ratio of the second sulfate to the second persulfate of at least 6:4 and a ratio of the amino acid to the second sulfate and the second persulfate combined of 1:2 to 2:1.

In one embodiment, wherein the stabilized oxygen-generating antiseptic composition includes the antiseptic mixture of the matrix of the first sulfate and a the first persulfate distributed in the matrix of the first sulfate, the ratio of the first sulfate to the first persulfate may be any suitable ratio, including, but not limited to, at least 8:2, alternatively at least 8.5:1.5, alternatively at least 9:1, alternatively at least 9.5:0.5, alternatively at least 9.7:0.3, alternatively at least 9.9:0.1, alternatively at least 9.95:0.05. In a further embodiment, the ratio of the first sulfate to the first persulfate, being at least any of the foregoing ratios, or subdivisions thereof, is less than 9.99999:0.00001, alternatively less than 9.9999:0.0001, alternatively less than 9.999:0.001, alternatively less than 9.99:0.01, alternatively less than 9.98:0.02, alternatively less than 9.97:0.03, alternatively less than 9.96:0.04.

The matrix of the first sulfate of the antiseptic mixture may be a crystalline matrix, a glassy matrix, an amorphous matrix, or combinations thereof. The first persulfate of the antiseptic mixture may be homogenously distributed throughout the matrix or heterogeneously distributed throughout the matrix.

In another embodiment, wherein the stabilized active oxygen-generating antiseptic composition includes the antiseptic polymer formed by the reaction of second sulfate, the second persulfate, and the amino acid in the reaction solution, the reaction solution may have any suitable ratio of the second sulfate to the second persulfate, including, but not limited to, at least 6:4, alternatively at least 7:3, alternatively at least 8:2, alternatively at least 8.5:1.5, alternatively between 6:4 to 9.99:0.01, or any subdivision thereof. The antiseptic polymer may form from the beginning the reaction, and the reaction to form the antiseptic polymer may be terminated once a desired molecular weight of the antiseptic polymer is reached and/or a desired pH of the reaction solution is reached.

The antiseptic polymer may have any suitable molecular weight, including, but not limited to, a molecular weight of less than 2,000 Daltons, alternatively less than 1,900 Daltons, alternatively less than 1,800 Daltons, alternatively less than 1,700 Daltons, alternatively less than 1,600 Daltons, alternatively less than 1,500 Daltons.

The ratio of the amino acid to the second sulfate and the second persulfate of the reaction solution combined may be any suitable ratio, including, but not limited to, 1:2 to 2:1, alternatively 1:1.5 to 1.5:1, alternatively 1:1.2 to 1.2:1, alternatively 1:1.1 to 1.1:1, alternatively 1:1.05 to 1.05:1, alternatively 1:1. The amino acid of the reaction solution may be any suitable amino acid, including, but not limited to, histidine, glutamine, alanine, aspartic acid, lysine, glycine, cysteine, arginine, proline, or combinations thereof.

The first sulfate of the antiseptic mixture, when present, and the second sulfate of reaction solution of the antiseptic polymer, when present, may be any suitable sulfate, including, but not limited to, $Li_2SO_4$, $Na_2SO_4$, $K_2SO_4$, $LiNaSO_4$, $LiKSO_4$, $NaKSO_4$, or combinations thereof.

The first persulfate of the antiseptic mixture, when present, and the second persulfate of the reaction solution of the antiseptic polymer, when present, may be any suitable persulfate, including, but not limited to, peroxomonosulfate. Suitable peroxomonosulfates include, but are not limited to, $LiHSO_5$, $NaHSO_5$, $KHSO_5$, $LiNaSO_5$, $LiKSO_5$, $NaKSO_5$, $Li_2SO_5$, $Na_2SO_5$, $K_2SO_5$, or combinations thereof.

The aforementioned first sulfates of the antiseptic mixture and first persulfates of the antiseptic mixture may be combined with one another in any combination. In one embodiment, the first sulfate includes $K_2SO_4$ and the first persulfate includes $KHSO_5$. In a further embodiment, the first sulfate consists of $K_2SO_4$ and the first persulfate consists of $KHSO_5$.

The aforementioned second sulfates, second persulfates, and amino acids of the reaction solution of the antiseptic polymer may be combined with one another in any suitable combination. In one embodiment, the second sulfate of the reaction solution includes $K_2SO_4$, the second persulfate of the reaction solution includes $KHSO_5$, and the amino acid of the reaction solution includes histidine. In a further embodiment, the second sulfate of the reaction solution consists of $K_2SO_4$, the second persulfate of the reaction solution consists of $KHSO_5$, and the amino acid of the reaction solution consists of histidine.

In one embodiment, the antiseptic composition includes both the antiseptic mixture and the antiseptic polymer. The second sulfate of the reaction solution of the antiseptic polymer may have the same chemical composition as the first sulfate of the antiseptic mixture or a distinct composition from the first sulfate of the antiseptic mixture. The second persulfate of the reaction solution of the antiseptic polymer may have the same chemical composition as the first persulfate of the antiseptic mixture or a distinct composition from the first persulfate of the antiseptic mixture. The first sulfate of the antiseptic mixture and the second sulfate of the reaction solution of the antiseptic polymer may have the same chemical composition while the first persulfate of the antiseptic mixture and the second persulfate of the reaction solution of the antiseptic polymer have distinct chemical compositions from one another. Alternatively, the first persulfate of the antiseptic mixture and the second persulfate of the reaction solution of the antiseptic polymer may have the same chemical composition while the first sulfate of the antiseptic mixture and the second sulfate of the reaction solution of the antiseptic polymer have distinct chemical compositions from one another. Alternatively, first persulfate of the antiseptic mixture and the second persulfate of the reaction solution of the antiseptic polymer may have the same chemical composition while the first sulfate of the antiseptic mixture and the second sulfate of the reaction solution of the antiseptic polymer have the same chemical composition. Alternatively, first persulfate of the antiseptic mixture and the second persulfate of the reaction solution of the antiseptic polymer may have distinct chemical compositions from one another while the first sulfate of the antiseptic mixture and the second sulfate of the reaction solution of the antiseptic polymer have distinct chemical compositions from one another.

The antiseptic mixture may be formed by dissolving a triple salt in a suitable solvent, such as, but not limited to, water, to form a solution, acid titrating the solution, performing solvent extraction on the solution, and then filtering the solution. Precipitate formed during this process may be dried to yield the antiseptic mixture in crystalline form. This antiseptic mixture in crystalline form may be used, directly applied as a solid or dissolved in a solvent to form an antiseptic irrigation solution. The remaining solution following recovery of the antiseptic mixture in crystalline form, which has a composition distinct from the dissolved triple salt, may be reacted with amino acid to form the antiseptic polymer. This antiseptic polymer may itself be used in its amorphous form or may be suspended in a solvent to form an antiseptic irrigation solution.

In one embodiment, an antiseptic irrigation solution includes a stabilized active oxygen-generating antiseptic composition and a solvent in which the stabilized active oxygen-generating antiseptic composition is dispersed. The antiseptic composition includes at least one of an antiseptic dispersal of the antiseptic mixture or the antiseptic polymer. With respect to the antiseptic dispersal of the antiseptic mixture, it is noted that the antiseptic dispersal would have the first sulfate and the first persulfate characterized by a ratio of the first sulfate to the first persulfate of at least 8:2, and as further described above, but that, as dispersed, the first sulfate may no longer constitute a matrix in which the first persulfate is distributed. In a further embodiment, the antiseptic composition includes both the antiseptic dispersal of the antiseptic mixture (the first sulfate and the first persulfate) as well as the antiseptic polymer.

Suitable solvents include, but are not limited to, water, aqueous solutions, biological fluids, wound exudate, blood plasma, or combinations thereof.

The concentration of the combined first sulfate and first persulfate in the solvent may be any suitable concentration, including, but not limited to, 0.01-100 mg/mL, alternatively 0.1-75 mg/mL, alternatively 0.1-10 mg/mL, alternatively 5-15 mg/mL, alternatively 10-20 mg/mL, alternatively 15-25 mg/mL, alternatively 20-30 mg/mL, alternatively 25-35 mg/mL, alternatively 30-40 mg/mL, alternatively 35-45 mg/mL, alternatively 40-50 mg/mL, alternatively 45-55 mg/mL, alternatively 50-60 mg/mL, alternatively 55-65 mg/mL, alternatively 60-70 mg/mL, alternatively 65-75 mg/mL, alternatively 70-80 mg/mL, alternatively 75-85 mg/mL, alternatively 80-90 mg/mL, alternatively 85-95 mg/mL, alternatively 90-100 mg/mL, or combinations or subdivisions thereof.

The antiseptic irrigation solution may have any suitable pH, including, but not limited to, a pH of 2.0-7.0; alternatively 2.5-6.5, alternatively 2.5-3.5, alternatively 3.0-4.0, alternatively 3.5-4.5, alternatively 4.0-5.0, alternatively 4.5-5.5, alternatively 5.0-6.0, alternatively 5.5-6.5, or combinations or subdivisions thereof.

The antiseptic irrigation solution may produce active oxygen for any suitable length of time following solvation of the antiseptic composition by the solvent, including, but not limited to, a period of at least 72 hours. In one embodiment, the antiseptic irrigation solution may produce active oxygen at a concentration of 0.01-1% based on the total antiseptic composition, alternatively 0.01-0.1%, alternatively 0.05-0.15%, alternatively 0.1-0.2%, alternatively 0.15-0.25%, alternatively 0.2-0.3%, alternatively 0.25-0.35%, alternatively 0.3-0.4%, alternatively 0.35-0.45%, alternatively 0.3-0.4%, alternatively 0.35-0.45%, alternatively 0.4-0.5%, alternatively 0.45-0.55%, alternatively 0.5-0.6%, alternatively 0.55-0.65%, alternatively 0.6-0.7%, alternatively 0.65-0.75%, alternatively 0.7-0.8%, alternatively 0.75-

0.85%, alternatively 0.8-0.9%, alternatively 0.85-0.95%, alternatively 0.9-1%, alternatively 0.1%, or combinations or subdivisions thereof.

In one embodiment, the antiseptic composition produces active oxygen at a lower rate and for a longer time than a comparative antiseptic irrigation solution having an equal amount (molar) of potassium peroxymonosulfate triple salt in lieu of the antiseptic composition and being otherwise identical.

The active oxygen produced by the antiseptic composition may include singlet $O_2$, ozone, superoxide, peroxide, or combinations thereof.

The antiseptic composition may further include amino acid dispersed in the solvent. Suitable amino acids which may be employed include, but are not limited to, histidine, glutamine, alanine, aspartic acid, lysine, glycine, cysteine, arginine, proline, or combinations thereof. The amino acid may be present at any suitable concentration, including, but not limited to, a concentration (based on the total antiseptic composition) of 1 mg/mL up to the solubility limit of the amino acid or amino acids dispersed therein, or combinations or subdivisions thereof.

In one embodiment, wherein the antiseptic composition including the antiseptic polymer rather than the antiseptic dispersal produces active oxygen at a lower rate and for a longer time relative to the antiseptic composition including the antiseptic dispersal rather than the antiseptic polymer at equal amounts (molar) the first sulfate to the second sulfate and the first persulfate to the second persulfate and being otherwise identical.

The stabilized oxygen-generating antiseptic compositions and antiseptic irrigation solutions disclosed herein may be used to treat surgical wounds, burns, lacerations, diabetic wounds, combat wounds, acute wounds, chronic wounds, and any other suitable wounds. The stabilized oxygen-generating antiseptic compositions may be applied directly to the wounds in particulate form or suspended in a suitable medium and may interact with biological fluids such as wound exudate and/or blood plasma to release active oxygen at a predetermined rate. Dissolved oxygen present in the antiseptic irrigation solutions may be released within the wound/operative site due to a change in pH (e.g. the antiseptic irrigation solution may have a pH of 4.0 whereas the wound bed would typically have an environmental pH of 6.5-7.0), altering the chemical equilibrium of the antiseptic irrigation solutions and releasing active oxygen to the wound tissue.

Without being bound by theory, it is noted that microbes produce a biofilm matrix including bacterial extracellular polysaccharide polymer protecting the bacteria within, and it is believed that the active oxygen produced by the stabilized oxygen-generating antiseptic compositions and antiseptic irrigation solutions formed therefrom depolymerize the biofilm protecting polysaccharide polymer structure by selective oxidation of glycosidic linkages to form glucose monomer and eradicate the bacteria within the biofilm. A mechanism for the oxidation of the glycosidic linkages in the polysaccharides is shown in FIG. 1.

In one embodiment, the bacteria, fungi, and viruses, against which the stabilized oxygen-generating antiseptic compositions and antiseptic irrigation solutions are effective, include *Staphylococcus Aureus* (MRSA), *Salmonella typhimurium*, *Pseudomonas aeruginosa*, *Klebsiella pneumonia*, *Acinetobacter baumannii*, *Escherichia coli*, *Enterococcus faecium*, *Enterobacter cloacae*, *Enterovacter aerogenes*, *Corynebacterium*, pseudodiptherium, *Corynebacterium* pseudodiptherium, *Candida albicans*, and Hepatitis A virus (HAv).

In one embodiment, an antiseptic article includes an article (having a surface) and at least one of a stabilized active oxygen-generating antiseptic composition or an oxygen-generating antiseptic coating formed from the stabilized active oxygen-generating antiseptic composition disposed on the surface of the article. The stabilized active oxygen-generating antiseptic composition includes at least one of the antiseptic mixture or the antiseptic polymer (both as further described above). The antiseptic article may include both the stabilized active oxygen-generating antiseptic composition and the oxygen-generating antiseptic coating formed from the stabilized active oxygen-generating antiseptic composition disposed on the surface of the article. The stabilized active oxygen-generating antiseptic composition may include both the antiseptic mixture and the antiseptic polymer.

The surface of the article on which the stabilized active oxygen-generating antiseptic composition, the oxygen-generating antiseptic coating formed from the stabilized active oxygen-generating antiseptic composition, or both is disposed may be an external surface of the article or an internal surface of the article, or both. In one embodiment, wherein the article includes a continuous porous substrate, the internal surface of the article on which the stabilized active oxygen-generating antiseptic composition, the oxygen-generating antiseptic coating formed from the stabilized active oxygen-generating antiseptic composition, or both is disposed is an internal continuous surface of the continuous porous substrate in fluid communication with an external surface of the article.

The oxygen-generating antiseptic coating may be covalently bonded, ionically bonded, or both to the surface of the article. The oxygen-generating antiseptic coating may be a monolayer or may have a plurality of layers.

In one embodiment, the stabilized active oxygen-generating antiseptic composition is applied to the surface of an article forming a monolayer coating that at least partially coats the article surface. Without being bound by theory, it is believed that the molecules on the monolayer coating have covalent or ionic or mixed chemical bonding characteristics under room temperature drying to form and adhere the monolayer coating to the implant surface. The level or degree of active molecule attachment may depend upon the properties and characteristics of the article surface (e.g., whether the surface is treated or untreated). In a further embodiment, the article surface undergoes a treatment that enhances or improves bonding and/or adherence of the stabilized active oxygen-generating antiseptic composition to the article surface. The treatment may be applied during manufacture or sterilization of the article. Suitable treatments include, but are not limited to, various treatments for enhancing the adherence or attachment of a coating to an uncoated surface, such as, but not limited to, gamma ray exposure.

The stabilized active oxygen-generating antiseptic composition in the form of a monolayer coating may be applied to the surface of an article using conventional coating techniques and apparatuses. Suitable coating techniques for use in the in the invention include, but are not limited to, dipping, brushing, and spraying. In one embodiment, an article is dipped into a solution of the stabilized active oxygen-generating antiseptic composition to form a monolayer coating on the article surface, and then the coated article is dried. Suitable drying techniques include, but are not limited to, conventional techniques and apparatuses for drying compositions applied to a substrate surface to form a coating. Dip-coating and then drying the coated article in a furnace and ambient atmosphere and pressure may produce a monolayer coating exhibiting improved antimicrobial properties relative to a monolayer coating produced without drying in a furnace. Without intending to be bound by theory, it is believed that use of a thermal activation process enhances the bonding of the monolayer to the article and yields a more robust monolayer of active molecules on the article surface relative to a process without active drying in a furnace.

The application or deposition of the stabilized active oxygen-generating antiseptic composition to form the monolayer coating and/or the drying process for the monolayer coating on the surface of the article when the article is an implant may be administered prior to, during, or after implantation of the implant into a patient body. In one embodiment, the surface treatment and/or monolayer coating and/or drying process is applied or deposited onto the implant surface while the implant is positioned or located outside of the body (i.e., prior to surgery). In another embodiment, the surface treatment and/or monolayer coating and/or drying process is applied or deposited onto the implant surface while the implant is being positioned/implanted inside of the body (i.e., during surgery). In yet another embodiment, the surface treatment and/or monolayer coating and/or drying process is applied or deposited onto the implant surface after the implant is positioned or located inside of the body, (i.e., following the implantation portion of surgery, but optionally prior to closure of the surgical site when the surgical site does not remain exposed at the completion of the surgery). The surface treatment and/or monolayer coating and/or drying process may be applied or deposited onto the implant surface of an uncoated implant that was previously positioned or located inside of the body (e.g., during a previous surgery) or the surface treatment and/or monolayer coating and/or drying process may be applied or deposited as a subsequent/additional coating (e.g., second coating) onto the implant surface of a coated implant that was previously positioned or located inside of the body (e.g., during a previous surgery).

In addition to the stabilized active oxygen-generating antiseptic compositions and irrigation solutions disclosed herein for use in forming a monolayer coating on the surface of an antiseptic article, there are additional conventional materials that are suitable for use in coating the surface of an antiseptic article such as an antiseptic implant which may be suitable for use in conjunction with the stabilized active oxygen-generating antiseptic compositions and irrigation solutions disclosed herein. Suitable conventional materials include, but are not limited to, antiseptics, disinfectants, germicides, antibacterials, and combinations thereof, such as, but not limited to, chlorhexidine.

The antiseptic article may be any suitable article, including, but not limited to, an implant, a grip, a lever, a knob, a latch, a handle, a door handle, a door knob, a counter, a countertop, a table, a tabletop, a bathtub, a sink, a shower, a plumbing fixture, a faucet, a faucent knob, a faucet handle, a toilet, a toilet handle, a urinal, a flushing lever, a keyboard, a phone, a mouse, a trackpad, a touchscreen, a steering wheel, a switch, a light switch, a button, a control lever, a control knob, a control stick, a gear shift, a tray table, a tray table latch, an armrest, a seat, a bed, a bed rail, a hospital bed, surgical equipment, operating room equipment, a floor, dental chair, a tray, dental equipment, optometry equipment, a contact lens, laboratory equipment, a gambling chip, a dye, gaming equipment, a slot machine, tools, safety equipment, or combinations thereof.

In one embodiment, the antiseptic article is an implant substrate configured to be surgically disposed in a living organism. The living organism may be, but is not limited to being, a human, a domesticated animal, a non-domesticated animal, or livestock.

Suitable implants include, but are not limited to, a hip implant, a dental implant, a knee implant, a spine implant, a shoulder implant, a joint implant, a spacer, a fixation accessory, a spinal interlaminal fixation accessory, a fascial anchor, a bone fixation anchor, a bone fixation accessory, a suture anchor, an aneurysm clip, an aneurysm coil, a nail fixation appliance, a blade fixation appliance, a plate fixation appliance, a spinal interlaminal fixation appliance, a spinal intervertebral body fixation appliance, a bolt, a bone grafting material, a dental bone grafting material, a synthetic bone grafting material, a clip, a breast clips, a hemostatic clip, a vascular clip, a vena cava clip, a breast implant, a bone cap, a pacemaker, a cardiac pacemaker, a cement obturator, a bone cement, an antibiotic bone cement, a pre-formed bone cement, a modular bone cement, a polymeric bone cement, a vertebroplasty bone cement, a cerclage fixation, a condylar plate fixation implant, a bone graft, a cranial bone graft, an autogenous cranial bone graft, a cranial bone allograft, a cranial bone xenograft, a craniotomy plate, a craniotomy mesh, a duraplasty material, a deep brain stimulator, an endosseous root form, a fixation fastener, a nondegradable fixation fastener, a soft tissue fixation fastener, an osteoinduction bone void filler, a fixation article, a fixation accessory, a fixation rod, a gastric pacemaker, a hemi humoral shoulder prosthesis, an orthodontic endosseous implant, a malar implant, a transmandibular implant, an arthrodesis interbody, a spinal strut graft, a vertebral body plate, a transpedicular screw, a transfacet screw, a vertebral fixation bar, a spinal stimulator, an internal chin prosthesis, an internal nose prosthesis, an intervertebral fusion device, a cervical intervertebral fusion device, a lumbar intervertebral fusion device, a solid-sphere lumbar intervertebral fusion device, an intracranial ventriculoperitoneal shunts and pressure probe, an intramedullary fixation rod, an intraocular lens implant, a contact lens, a lid weight, a scleral band, intravitreal silicone oil, an intraoral implant, an intraosseous implant, an intraossesous screw, a long term indwelling catheter, a malleable ligature, a malleable lock, a malleable wire, a maxillofacial prosthesis, a nose maxillofacial prosthesis, an ear maxillofacial prosthesis, an orbit maxillofacial prosthesis, an ossicular prosthesis, a cochlear implant, a metal stent, a bone fixation nail, a non-resorbable polyethyene terephthalate membrane, a non-resorbable polyethyene terephthalate oral cavity membrane, a nut, an oral cavity bone graft, an autogenous oral cavity bone graft, an oral cavity bone allograft, an oral cavity bone xenograft, an oral cavity guided tissue regenerative component, a collagen oral cavity guided tissue regenerative component, a pericardium oral cavity guided tissue regenerative component, an oral cavity guided tissue regenerative component, an orthopedic graft, an autogenous orthopedic graft, an orthopedic allograft, an orthopedic xenograft, an ossicular prosthesis, a partial ossicular replacement, a patello/femoral, semi-constrained, cemented, metal/polymer, a rigid rod penis implant, a peripheral nerve stimulator, a peritoneal dialysis implant, a peritoneal implant, a piercing, an earring piercing, a bar piercing, a pin, a fixation pin, a smooth fixation pin, a threaded fixation pin, a bone plate, a bone growth plate, a control bone growth plate, a pediatric bone growth plate, an epiphysiodesis bone growth plate, a bone fixation plate, a non-spinal bone fixation plate, a semi-rigid fixation plate, a semi-rigid fixation screw, a semi-rigid fixation head plate, a semi-rigid fixation head screw, a semi-rigid fixation face plate, a semi-rigid fixation face screw, a semi-rigid fixation skull base plate, a semi-rigid fixation skull base screw, a proximal femoral fixation implant, an oral cavity barrier membrane, a resorbable oral cavity barrier membrane, a non-resorbable oral cavity barrier membrane, a suture material, a resorbable suture material, a non-resorbable suture material, a fixation rod, a collapsible fixation rod, a non-collapsible fixation rod, an intramedullary fixation rod, a collapsible intramedullary fixation rod, a non-collapsible intramedullary fixation rod, a subperiosteal replacement prosthesis, a total prosthesis, a bone fixation screw, a spinal bone fixation screw, a non-spinal bone fixation screw, an autogenous spinal bone graft, a spinal bone allograft, a spinal bone xenograft, a spinal cord stimulator, a spinal implant fixation device, a staple, a bone fixation staple, a surgical mesh, a surgical stent, a suture, an absorbable suture, a non-absorbable suture, an external fixator system, an internal stape urgical, a temporomandibular joint prosthetic joint, a temporomandibular joint fossa prosthetic component, a titanium oral cavity reconstruction mesh, a titanium head and neck mesh, an ureteral catheter, a venooclussive material, a washer, a wire, an acetabular hip prosthesis a constrained cemented elbow prosthesis, a cemented semi constrained elbow prosthesis, a knee prosthesis, a hemi-knee prosthesis, a tibial knee prosthesis, a resurfacing knee prosthesis, a semi-constrained cemented ankle prosthesis, a temporary mandibular condyle prosthesis, an elbow prosthesis, a radial elbow prosthesis, a hemi-elbow prosthesis, a facial mandibular implant prosthesis, a constrained finger prosthesis, a finger prosthesis, a restrictor hip prosthesis, a constrained hip prosthesis, a femoral component hip prosthesis, a resurfacing femoral hip prosthesis, a femoral hemi-hip prosthesis, a femoral ball hemi-hip prosthesis, a femoral hemi-hip prosthesis, a femoral trunnion bearing hemi-hip prosthesis, a semi-constrained hip prosthesis, a semi-constrained partial patellofemorotibial knee prosthesis, a femorotibial knee prosthesis, a constrained femorotibial knee prosthesis, a non-constrained femorotibial knee prosthesis, a semi-constrained femorotibial knee prosthesis, a trunnion-bearing semi-constrained femorotibial knee prosthesis, an unicompartmental/unicondylar semi-constrained femorotibial knee prosthesis, a patellar resurfacing hemi-knee prosthesis, a non-constrained knee prosthesis, a patello/femorotibial knee prosthesis, a constrained patello-femorotibial knee prosthesis, a semi-constrained patello-femorotibial knee prosthesis, a rib replacement prosthesis, a shoulder prosthesis, a non-constrained shoulder prosthesis, a semi-constrained shoulder prosthesis, a shoulder prosthesis, a passive tendon prosthesis, a semi-constrained metatarsophalangeal toe joint prosthesis, a constrained toe prosthesis, a phalangeal hemi-toe prosthesis, an upper femoral prosthesis, a semi-constrained wrist prosthesis, a 2-part articulation semi-constrained wrist prosthesis, a 3-part articulation semi-constrained wrist prosthesis, a carpal lunate wrist prosthesis, a carpal scaphoid wrist prosthesis, an ulnar hemi-wrist prosthesis, a femorotibial knee prosthesis, a semi-constrained wrist prosthesis, a single use prosthesis, a carrier membrane, a surgical reconstruction carrier membrane, a body cavity surgical reconstruction carrier membrane, an oral cavity surgical reconstruction carrier membrane, a barrier membrane, a surgical reconstruction barrier membrane, a body cavity surgical reconstruction barrier membrane, an oral cavity surgical reconstruction barrier membrane, a scaffolding membrane, a surgical reconstruction scaffolding membrane, a body cavity surgical reconstruction scaffolding membrane, an oral cavity surgical reconstruction scaffolding membrane, a porous membrane, a surgical reconstruction porous membrane, a body cavity surgical reconstruction porous membrane, an oral cavity surgical reconstruction porous membrane, a semi-porous membrane, a surgical reconstruction semi-porous membrane, a body cavity surgical reconstruction semi-porous membrane, an oral cavity surgical reconstruction semi-porous membrane, a collagen membrane, a surgical reconstruction collagen membrane, a body cavity surgical reconstruction collagen membrane, an oral cavity surgical reconstruction collagen membrane, an allograft membrane, a surgical reconstruction allograft membrane, a body cavity surgical reconstruction allograft membrane, an oral cavity surgical reconstruction allograft membrane, allograft bone, surgical reconstruction allograft bone, body cavity surgical reconstruction allograft bone, oral cavity surgical reconstruction allograft bone, autogenous bone, surgical reconstruction autogenous bone, body cavity surgical reconstruction autogenous bone, oral cavity surgical reconstruction autogenous bone, synthetic grafting, tissue regenerating synthetic grafting, body cavity tissue regenerating synthetic grafting, oral cavity tissue regenerating synthetic grafting, allogenic grafting, allogenic tissue regenerating grafting, allogenic body cavity tissue regenerating grafting, allogenic oral cavity tissue regenerating grafting, autogenous grafting, autogenous tissue regenerating grafting, autogenous body cavity tissue regenerating grafting, autogenous oral cavity tissue regenerating grafting, healing materials for extraction sockets, bony defects, or soft tissue defects, synthetic healing materials for extraction sockets, bony defects, or soft tissue defects, allogenic healing materials for extraction sockets, bony defects, or soft tissue defects, autogenous healing materials for extraction sockets, bony defects, or soft tissue defects, healing materials for body cavity extraction sockets, bony defects, or soft tissue defects, healing materials for oral cavity extraction sockets, bony defects, or soft tissue defects, healing materials for irradiated bone, bone subject to medication related bone changes or changes relating to systematic illness or disease, synthetic healing materials for healing materials for irradiated bone, bone subject to medication related bone changes or changes relating to systematic illness or disease, allogenic healing materials for healing materials for irradiated bone, bone subject to medication related bone changes or changes relating to systematic illness or disease, autogenous healing materials for healing materials for irradiated bone, bone subject to medication related bone changes or changes relating to systematic illness or disease, a mesh reconstructive alloy that acts as a container or scaffolding to promote healing or bone growth, a titanium mesh reconstructive alloy that acts as a container or scaffolding to promote healing or bone growth, a disinfectant membrane, a healing membrane, a disinfectant material, a healing material, a biological material, a medical material, or combinations thereof.

The implant may be made from any suitable material, including, but not limited to, polymers, ultra-high-molecular-weight polyethylenes, polytetrafluoroethylene, ceramics, metals, alloys, steels, stainless steels, titanium, titanium alloys, concrete, composites, polyacetal, porous materials, calcium phosphate, non-porous materials, cemented materials, non-cemented materials, osteophilic finished materials, biological materials, biologically-derived materials, composites having biological materials, composites having biologically-derived materials, or combinations thereof.

In one embodiment, an oral lavage includes the antiseptic irrigation solution as disclosed above. Oral usage of the oral lavage may eradicate a broad spectrum of bacteria, viruses, and fungi for chronic dental diseases such as, but not limited to, periodontitis, infected pulp, abscesses, and canker sores. Oral application of the oral lavage may promote natural tooth repair in regenerative dentistry such as regenerative endodontics, soft tissue regeneration, or bone regeneration.

In one embodiment, a dermatological composition includes the stabilized oxygen-generating antiseptic composition or antiseptic irrigation solution as disclosed above. The dermatological composition may be a dry powder, a mask, a liquid composition, a cream, an emulsion, or any other suitable format. Topical application of the dermatological composition may reduce or eliminate facial tissue infection such as, but not limited to, acne, or may provide oxygen-based regeneration of facial tissue.

In one embodiment, a respiratory treatment composition includes the stabilized oxygen-generating antiseptic composition or antiseptic irrigation solution as disclosed above. The respiratory treatment composition may be a dry powder, a vapor, or a liquid composition. Application of the respiratory treatment composition may reduce or eliminate a broad spectrum of bacteria, viruses, fungi, or biofilms associated with chronic obstructive conditions such as, but not limited to, cystic fibrosis, asthma, or emphysema, may reduce or eliminate nasal infections, or may promote repair or regeneration of lung tissue.

In one embodiment, a cardiovascular treatment composition includes the stabilized oxygen-generating antiseptic composition or antiseptic irrigation solution as disclosed above. Application of the cardiovascular treatment composition may provide coronary oxygenation or tissue regeneration when delivered in liquid injection directly to damaged heart muscle tissue, may provide oxygenation of damaged heart tissue for decreased recovery time, may regenerate cardiac muscle, may promote formations of new blood vessels, may inhibit or prevent infection, or may reduce or eliminate inflammation of cardiac muscle.

In one embodiment, an eyedrop or eye wash composition includes the stabilized oxygen-generating antiseptic composition or antiseptic irrigation solution as disclosed above. Application of the eyedrop or eye wash composition may reduce or eliminate eye infection or provide eye disease therapy for diabetic retinopathy.

In one embodiment, an oxygenation composition includes the stabilized oxygen-generating antiseptic composition or antiseptic irrigation solution as disclosed above. Application of the oxygenation composition may accelerate treatment of concussions or strokes.

In one embodiment, a beverage includes the stabilized oxygen-generating antiseptic composition or antiseptic irrigation solution as disclosed above. Imbibing the beverage may change the population of bacteria via selection pressure.

EXAMPLES

The principles of the invention are demonstrated with respect to the following examples, which are presented by way of exemplification only and not intended in any way to limit the more general teachings described herein.

Oxygen Delivery Time Kill Test for ESKAPE Pathogens:
*Enterobacter aerogenes* ATCC 13048
*Staphylococcus aureus* ATCC 43300 (MRSA)
*Klebsiella pneumoniae* ATCC 13883
*Acinetobacter baumannii* (clinical isolate)
*Pseudomonas aeruginosa* ATCC 27853
*Enterococcus faecium* (VRE clinical isolate)

A stabilized oxygen-generating antiseptic composition was prepared and dissolved at a concentration of 1 mg/mL in aqueous suspensions of cultures at a density of approximately $5\times10^5$ cfu/mL. The stabilized oxygen-generating antiseptic composition was characterized by a sulfate to persulfate ration of 9.7:0.3, with the sulfate being $K_2SO_4$ and the persulfate being $KHSO_5$. The stabilized oxygen-generating antiseptic composition was free of amino acids, and produced 0.1% active oxygen in the resulting solution, as measured by iodometric titration. At intervals, samples were removed, diluted through D/E neutralizing broth, and spread onto plates of D/E neutralizing agar. Plates were incubated for 24-48 hours at 35° C.

For the Gram-negative cultures, *A. baumannii*, *E. aerogenes*, *K. pneumoniae*, and *P. aeruginosa*, viable count declined over 15 minutes to where the experiment could not measure it (<100 CFU/mL).

For *S. aureus*, viable count declined approximately 98% over 30 minutes (in one experiment, from $4.2\pm0.4\times10^5$ cfu/mL to $7.4\pm1.4\times10^3$ cfu/mL). For *E. faecium*, which was the most tolerant, viable count declined approximately 97% over 30 minutes.

Testing demonstrated successful in-vitro eradication of planktonic and biofilm populations of MRSA and *P. aeruginosa*. Percent killing and $Log_{10}$ reduction of *P. aeruginosa* (ATCC 27853) and MRSA (ATCC 35984) biofilms by antiseptic irrigation solution was performed according to Minimum Biofilm Eradication Concentration (MBEC) Assay® protocol. The results of this testing are shown in Table 1.

TABLE 1

| MBEC Assay ® Testing Results | | | | |
|---|---|---|---|---|
| | % Kill | LogR | Ttest | S/NS |
| *P. aeruginosa* | | | | |
| Biofilm | | | | |
| 45 mg/mL | 100.00% | 5.02 | 0.00 | S |
| 10 mg/mL | 100.00% | 5.02 | 0.00 | S |
| Planktonic | | | | |
| 45 mg/mL | 100.00% | 6.41 | 0.00 | S |
| 10 mg/mL | 100.00% | 6.41 | 0.00 | S |
| MRSA | | | | |
| Biofilm | | | | |
| 45 mg/mL | 100.00% | 5.33 | 0.00 | S |
| 10 mg/mL | 91.34% | 1.06 | 0.00 | S |
| Planktonic | | | | |
| 45 mg/mL | 100.00% | 6.55 | 0.00 | S |
| 10 mg/mL | 100.00% | 4.58 | 0.00 | S |

Figure 2:
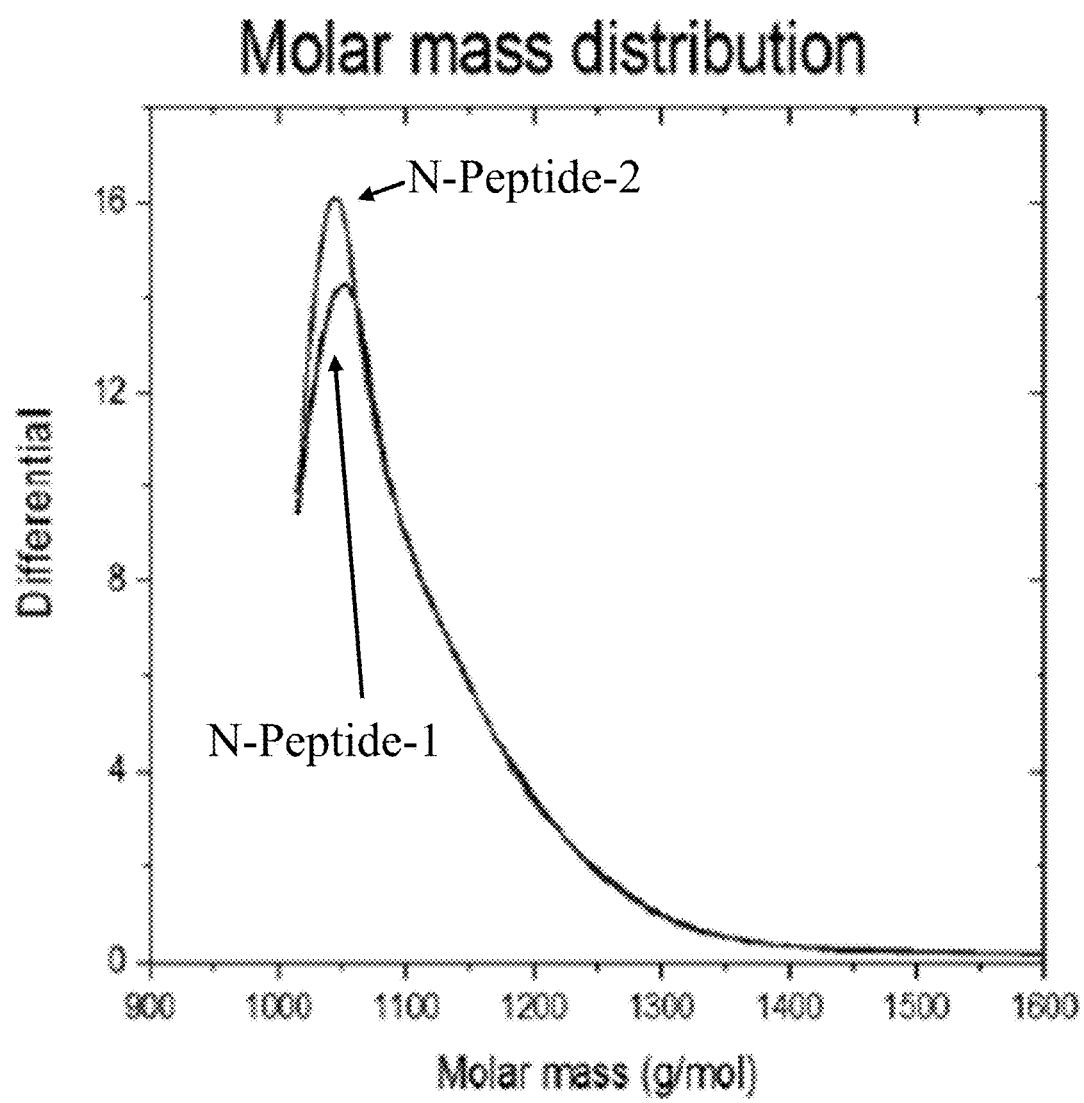
FIG. 2 shows the molar mass distribution of a polymer measured by asymmetric field-flow FFF technique, according to an embodiment of the invention.

An exemplary stabilized oxygen-generating antiseptic composition including the polymer was analyzed by asymmetric field-flow fractionation (FFF) technique with a UV detector comprising of sulfate/persulfate-histidine polymer produced at a pH of 6.0, which measured a molecular weight of approximately 1,500 Daltons, as shown in FIG. 2. FFF is a family of separation techniques developed for small molecule weight measurements. In the present context, FFF provides high resolution separation of any particulate matter from 1 nm up to 100 μm in a liquid medium.

Figure 3:
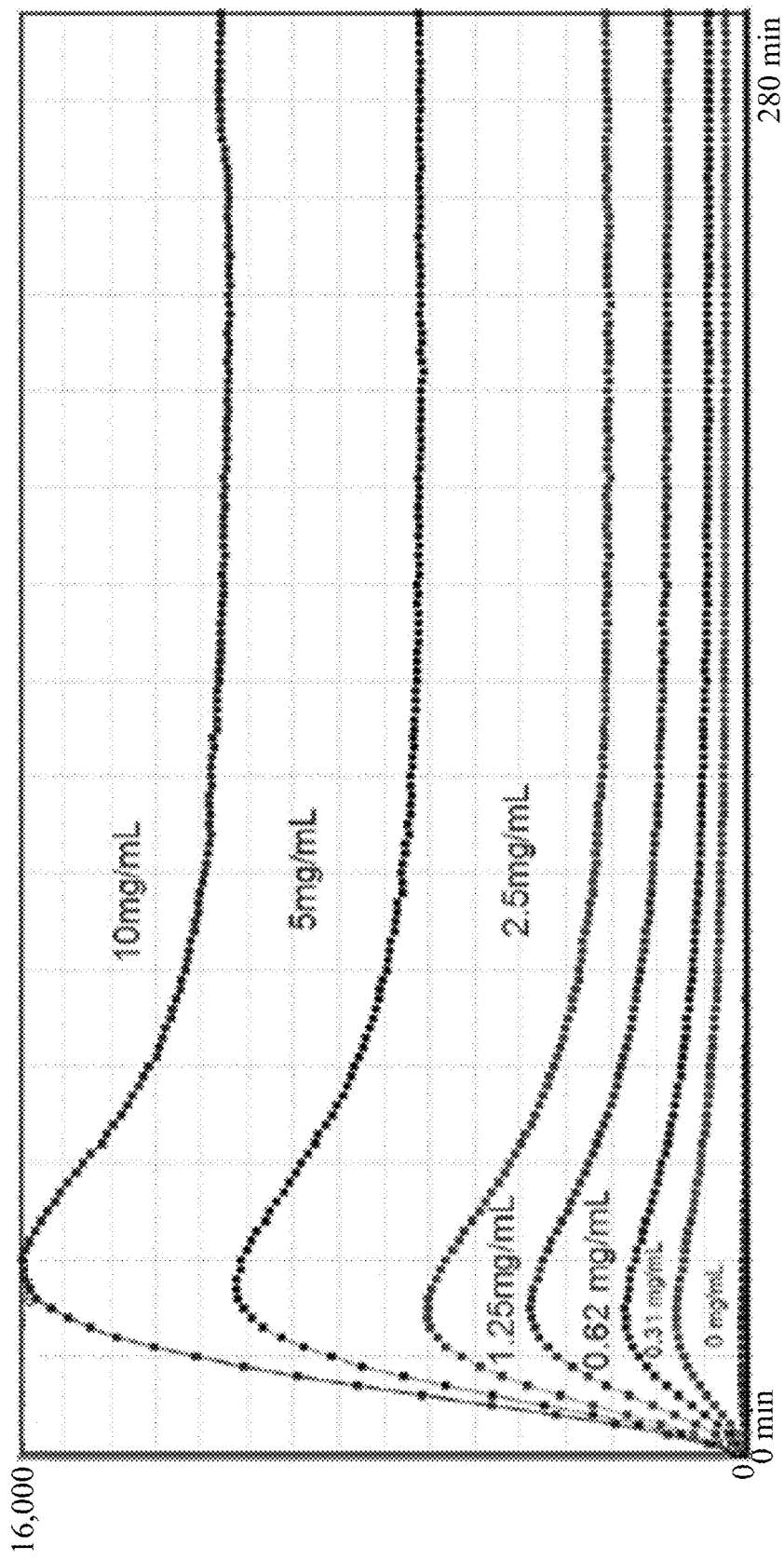
FIG. 3 shows chemiluminescence measurements for active oxygen production evaluated by Beckman Coulter of an antiseptic irrigation solution, according to an embodiment of the invention.

As reported in FIG. 3, oxygen delivery for an antiseptic irrigation solution was measured by chemiluminescence evaluated by Beckman Coulter. Testing results were obtained by dissolving freeze dried powder of a stabilized oxygen-generating antiseptic composition in water and measuring its stability over 5 hours against Lumigen HyPerBlu die at different concentration and at PH of 9.3. The results indicate that the antiseptic irrigation solution was stable and delivered active oxygen for 5 hours continuously for different concentrations. This antiseptic irrigation solution was prepared by dissolving 1,500 Dalton molecular weight polymer comprising sulfate/persulfate-histidine in water with different concentrations up to 10 mg/mL as indicated in FIG. 3.

Time-to-kill testing was performed on an exemplary stabilized oxygen-generating antiseptic composition including the polymer against drug-resistant bacteria (*P. aeruginosa*; ATCC BAA-2108), the results of which testing is presented in Table 2. The antiseptic composition (TS) was a powder of sulfate/persulfate-histidine polymer and was dispersed in water at a concentration of 45 mg/L for the time-to-kill testing.

TABLE 2

Time-to-Kill Testing for *P. aeruginosa* (ATCC BAA-2108)

| Contact Time | Test Substance | CFU/mL | Average Percent Reduction Compared to Control at Time Zero | Average Log$_{10}$ Reduction Compared to Control at Time Zero |
|---|---|---|---|---|
| Time Zero | Control | 2.85E+06 | | N/A |
| 1 hour | Parallel Control | 3.20E+06 | | N/A |
| 1 hour | TS 45 mg/L | 2.40E+06 | 25.00% | 0.12 |
| 2 hours | Parallel Control | 3.05E+06 | | N/A |
| 2 hours | TS 45 mg/L | 1.30E+06 | 57.38% | 0.37 |
| 3 hours | Parallel Control | 2.70E+06 | | N/A |
| 3 hours | TS 45 mg/L | 5.00E+05 | 81.48% | 0.73 |
| 4 hours | Parallel Control | 3.10E+06 | | N/A |
| 4 hours | TS 45 mg/L | 2.20E+05 | 92.92% | 1.15 |
| 5 hours | Parallel Control | 4.75E+06 | | N/A |
| 5 hours | TS 45 mg/L | 8.85E+04 | 98.14% | 1.73 |

Animal Studies:

Referring to FIGS. 4(a) and 4(b), stabilized oxygen-generating antiseptic composition in powder form was dissolved in deep wounds in porcine tissue with no evidence of local or systemic toxicity. Wound heading was significantly accelerated comparted to controls.

Figure 5:
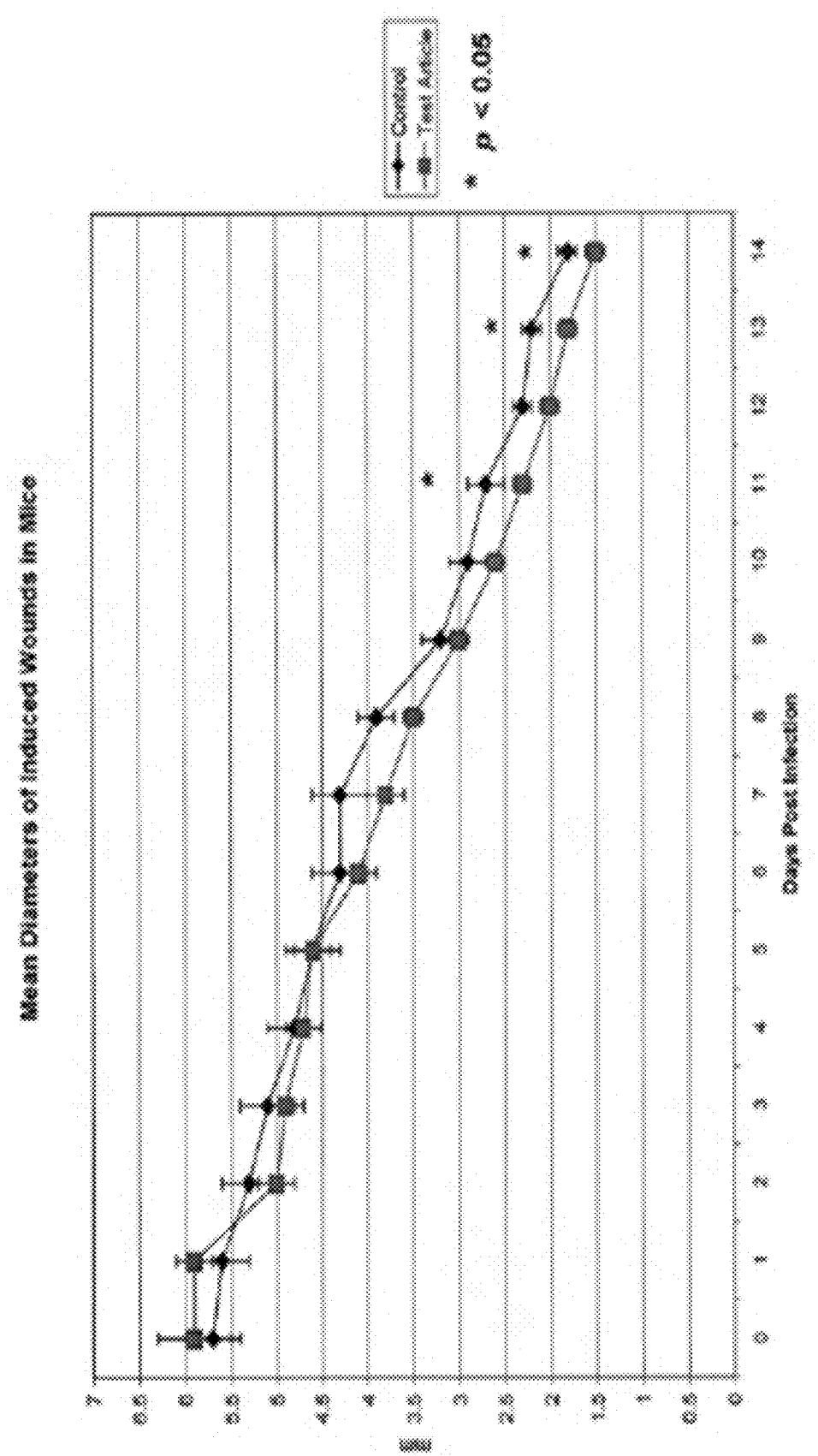
FIG. 5 shows the acceleration of wound healing in mice wounds inoculated with MRSA with treatment by stabilized oxygen-generating antiseptic composition in powder form dissolved in the wounds, according to an embodiment of the invention.

Referring to FIG. 5, treatment by stabilized oxygen-generating antiseptic composition in powder form dissolved in deep wounds in mice tissue inoculated with MRSA shows no evidence of local or systemic toxicity as well as significant acceleration compared to controls (no treatment).

Testing Protocols:

Time-to-Kill Testing: A time-to-kill study measures the antimicrobial activity of the tested product over time (complies with ASTM Standard E 2315-03).

Biofilm Testing for Oxygen Delivery Chemistry: Evaluated by (ATCC 35984) MBEC Assay® Protocol.

Oxygen Delivery Powder Stability Performance Chart.

Cytotoxicity Testing by MEMS Elution Test: Minimal Essential Media (MEMS) Elution Testing was performed by Nelson Laboratories for oxygen delivery base cytotoxicity of extractable substances with passing score. The MEMS elution assay or elution test is an in vitro cytotoxicity assay designed to show the presence of toxic material eluted from a test sample as it affects L929 cells cultured in the presence of the extract. Extracts of test articles are applied to L929 cells.

X-ray Powder Diffraction (XRD): Used primarily for phase identification of oxygen delivery chemistry.

ATR-FTIR Attenuated Total Reflection (ATR): Sampling technique used to identify functional chemical groups associated with oxygen delivery chemistry.

Lumigen HyPerBlu Technology: Reagent which is a novel chemiluminescent substrate that accurately and directly measures the activity of oxygen in solution.

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A stabilized active oxygen-generating antiseptic composition, comprising an antiseptic mixture including:
   a matrix of a first sulfate; and
   a first persulfate distributed in the matrix of the first sulfate,
   wherein the antiseptic mixture, including both the matrix of the first sulfate and the first persulfate distributed in the matrix of the first sulfate, is a co-precipitate in crystalline form characterized by a molar ratio of the first sulfate to the first persulfate of at least 8:2 and the first persulfate is a peroxomonosulfate.

2. The antiseptic composition of claim 1, wherein the first sulfate is selected from the group consisting of Li$_2$SO$_4$; Na$_2$SO$_4$; K$_2$SO$_4$; LiNaSO$_4$; LiKSO$_4$; NaKSO$_4$, and combinations thereof.

3. The antiseptic composition of claim 2, wherein the first sulfate is K$_2$SO$_4$.

4. The antiseptic composition of claim 1, wherein the peroxomonosulfate of the first persulfate is selected from the group consisting of LiHSO$_5$; NaHSO$_5$; KHSO$_5$; LiNaSO$_5$; LiKSO$_5$; NaKSO$_5$, Li$_2$SO$_5$; Na$_2$SO$_5$; K$_2$SO$_5$, and combinations thereof.

5. The antiseptic composition of claim 4, wherein the peroxomonosulfate of the first persulfate is KHSO$_5$.

6. The antiseptic composition of claim 1, wherein the molar ratio of the first sulfate to the first persulfate is at least 9:1.

7. The antiseptic composition of claim 1, wherein the first persulfate is homogenously distributed throughout the matrix of the first sulfate.

8. The antiseptic composition of claim 1, wherein the antiseptic composition further includes an antiseptic polymer formed by the reaction of a second sulfate, a second persulfate, and amino acid in a reaction solution having a molar ratio of the second sulfate to the second persulfate of at least 6:4 and a molar ratio of the amino acid to the second sulfate and the second persulfate combined of 1:2 to 2:1.

9. The antiseptic composition of claim 8, wherein the antiseptic polymer includes a molecular weight of less than 2,000 Daltons.

10. The antiseptic composition of claim 8, wherein the molar ratio of the amino acid to the second sulfate and the second persulfate combined is 1:1.1 to 1.1:1.

11. The antiseptic composition of claim 8, wherein the amino acid is selected from the group consisting of histidine, glutamine, alanine, aspartic acid, lysine, glycine, cysteine, arginine, proline, and combinations thereof.

12. The antiseptic composition of claim 11, wherein the amino acid is histidine.

13. The antiseptic composition of claim 8, wherein the second sulfate has the same chemical composition as the first sulfate.

14. The antiseptic composition of claim 8, wherein the second persulfate has the same chemical composition as the first persulfate.

15. The antiseptic composition of claim 8, wherein the second sulfate has a distinct chemical composition from the first sulfate.

16. The antiseptic composition of claim 8, wherein the second persulfate has a distinct chemical composition from the first persulfate.

17. An antiseptic article, comprising:
an article having a surface; and
at least one of:
a stabilized active oxygen-generating antiseptic composition; or
an oxygen-generating antiseptic coating formed from the stabilized active oxygen-generating antiseptic composition,
disposed on the surface of the article,
wherein the stabilized active oxygen-generating antiseptic composition includes an antiseptic mixture including:
a matrix of a first sulfate; and
a first persulfate distributed in the matrix of the first sulfate,
wherein the antiseptic mixture, including both the matrix of the first sulfate and the first persulfate distributed in the matrix of the first sulfate, is a co-precipitate in crystalline form characterized by a molar ratio of the first sulfate to the first persulfate of at least 8:2 and the first persulfate is a peroxomonosulfate.

18. The antiseptic article of claim 17, wherein the surface is an external surface of the article and the antiseptic coating formed from the stabilized active oxygen-generating antiseptic composition is present.

19. The antiseptic article of claim 18, wherein the oxygen-generating antiseptic coating is a monolayer.

20. The antiseptic article of claim 18, wherein the oxygen-generating antiseptic coating is covalently bonded, ionically bonded, or both to the surface of the article.

21. The antiseptic article of claim 17, wherein the article includes a continuous porous substrate and the surface is an internal continuous surface of the continuous porous substrate in fluid communication with an external surface of the article.

22. The antiseptic article of claim 17, wherein the antiseptic article is an implant substrate configured to be surgically disposed in a living organism.

23. The antiseptic article of claim 17, wherein the stabilized active oxygen-generating antiseptic composition further includes an antiseptic polymer formed by the reaction of a second sulfate, a second persulfate, and amino acid in a reaction solution having a molar ratio of the second sulfate to the second persulfate of at least 6:4 and a molar ratio of the amino acid to the second sulfate and the second persulfate combined of 1:2 to 2:1.

24. The antiseptic composition of claim 8, wherein the second sulfate is selected from the group consisting of $Li_2SO_4$; $Na_2SO_4$; $K_2SO_4$; $LiNaSO_4$; $LiKSO_4$; $NaKSO_4$, and combinations thereof.

25. The antiseptic composition of claim 24, wherein the second sulfate is $K_2SO_4$.

26. The antiseptic composition of claim 8, wherein the peroxomonosulfate of the second persulfate is selected from the group consisting of $LiHSO_5$; $NaHSO_5$; $KHSO_5$; $LiNaSO_5$; $LiKSO_5$; $NaKSO_5$, $Li_2SO_5$; $Na_2SO_5$; $K_2SO_5$, and combinations thereof.

27. The antiseptic composition of claim 26, wherein the peroxomonosulfate of the second persulfate is $KHSO_5$.

* * * * *